United States Patent
Bae et al.

(10) Patent No.: US 9,647,219 B1
(45) Date of Patent: May 9, 2017

(54) N-DOPED NANOCARBON MATERIALS AND METHOD FOR MANUFACTURING THE SAME

(71) Applicant: Korea Institute of Science and Technology, Seoul (KR)

(72) Inventors: Sukang Bae, Wanju-gun (KR); Byung Joon Moon, Wanju-gun (KR); Ye Lin Oh, Wanju-gun (KR); Dongheon Shin, Wanju-gun (KR); Sang Jin Kim, Wanju-gun (KR); Sang Hyun Lee, Wanju-gun (KR); Tae-Wook Kim, Wanju-gun (KR); Dong Su Lee, Wanju-gun (KR); Min Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/297,653

(22) Filed: Oct. 19, 2016

(30) Foreign Application Priority Data

Oct. 20, 2015 (KR) .................... 10-2015-0146186
Aug. 26, 2016 (KR) .................... 10-2016-0109301

(51) Int. Cl.
| | | |
|---|---|---|
| *C07D 471/22* | (2006.01) | |
| *H01L 51/42* | (2006.01) | |
| *H01L 51/00* | (2006.01) | |
| *H01L 31/0352* | (2006.01) | |
| *H01L 31/0256* | (2006.01) | |

(52) U.S. Cl.
CPC ........ *H01L 51/0072* (2013.01); *C07D 471/22* (2013.01); *H01L 31/035218* (2013.01); *H01L 51/42* (2013.01); *H01L 2031/0344* (2013.01)

(58) Field of Classification Search
CPC ....... C07D 471/22; H01L 51/42; H01L 51/00; H01L 31/0352
See application file for complete search history.

(56) References Cited

U.S. PATENT DOCUMENTS

2015/0280248 A1  10/2015  Tour et al.
2015/0284318 A1  10/2015  Zhao et al.
2015/0298977 A1  10/2015  Yoon

FOREIGN PATENT DOCUMENTS

| CN | 104059644 | * | 9/2014 | ............ C09K 11/65 |
|---|---|---|---|---|
| KR | 10-2014-0065275 A | | 5/2014 | |
| KR | 10-1403534 B1 | | 6/2014 | |
| KR | 10-2015-0090605 A | | 8/2015 | |
| KR | 10-1556584 B1 | | 10/2015 | |

OTHER PUBLICATIONS

Pan, Dengyu, et al. "Hydrothermal Route for Cutting Graphene Sheets Into Blue-Luminescent Graphene Quantum Dots,"*Advanced Materials* 22.6 (2010): 734-738. (5 pages, in English).
Peng, Juan, et al. "Graphene Quantum Dots Derived From Carbon Fibers," *Nano letters* 12.2 (2012): 844-849. (6 pages, in English).
Tang, Libin, et al. "Deep Ultraviolet Photoluminescence of Water-Soluble Self-Passivated Graphene Quantum Dots," *ACS Nano* 6.6 (2012): 5102-5110. (9 pages, in English).
Wu, Xu, et al. "Fabrication of Highly fluorescent Graphene Quantum Dots Using L-Glutamic Acid For In Vitro/In Vivo Imaging and Sensing." *Journal of Materials Chemistry C* 1.31 (2013): 4676-4684. (9 pages, in English).

* cited by examiner

*Primary Examiner* — Erich A Leeser
(74) *Attorney, Agent, or Firm* — NSIP Law

(57) ABSTRACT

Provided are nitrogen-doped carbon quantum dots as pyrolysis product of fumaronitrile. The carbon quantum dots may be formed in such a manner that nitrogen may be doped in an amount of 3-10 wt % based on the total weight of the carbon quantum dots with no need for a separate doping process. As a result, the carbon quantum dots have excellent properties, such as optical property, electroconductivity and thermal safety, and thus may be useful for photocatalysts or organic solar cells, or the like.

10 Claims, 23 Drawing Sheets

Citric acid
(CA)

L-glutamic acid
(GA)

Glucose
(GC)

Fumaronitrile
(FN)

N-DOPED NANOCARBON MATERIALS AND METHOD FOR MANUFACTURING THE SAME

CROSS-REFERENCE TO RELATED APPLICATION

This application claims priority to Korean Patent Application No. 10-2015-0146186, filed on Oct. 20, 2015 and Korean Patent Application No. 10-2016-0109301, filed on Aug. 26, 2016, and all the benefits accruing therefrom under 35 U.S.C. §119, the contents of which in its entirety are herein incorporated by reference.

BACKGROUND

1. Field

The present disclosure relates to nitrogen-doped carbon quantum dots and a method for producing the same. More particularly, the present disclosure relates to nitrogen-doped carbon quantum dots obtained by using a single process and a method for producing the same.

2. Description of the Related Art

Since a carbon-based material having a soccer ball-like structure, called fullerene, was discovered in 1985, various structures having excellent physical, chemical and electrical properties have been produced and discovered, such structures including graphene, carbon nanotubes, carbon nanocones, carbon nanoonions, carbon nanorings and carbon quantum dots having the smallest size of several nanometers. Carbon quantum dots do not have a complete carbon crystal shape but are nanometer-scaled carbon structures having unique physical and optical properties. Such carbon quantum dots are shown to have high applicability in various industrial fields, and thus they have been studied intensively. Particularly, carbon quantum dots with a nanometer-scaled size have semiconductive properties, and thus show fluorescence properties varied with particle sizes and functional groups at the edges thereof. In addition, carbon quantum dots show different fluorescence properties at different wavelengths of excitation light. Further, since carbon quantum dots have no transition metal, they are eco-friendly materials and are expected to be studied about their applications in the future.

However, although carbon quantum dots have high applicability in various industrial fields, their preparation according to the related art includes a complicated process due to purification and separation, requires a lot of time, and provides low yield. Thus, studies about application of carbon quantum dots are limited. In addition, there is a difficulty in separating acid used for forming carbon quantum dots having a very small size. Moreover, a high-temperature process or harmful material is used during the reduction of oxidized carbon nanomaterials. Therefore, there is a need for preparing eco-friendly carbon quantum dots to solve the above-mentioned problems.

REFERENCES

Patent Documents (Patent Document 1) KR10-2014-0065275 A
(Patent Document 2) KR10-1403534 B1

Non-Patent Documents (Non-Patent Document 1) Peng, Juan, et al. "Graphene quantum dots derived from carbon fibers." Nano letters 12.2 (2012): 844-849.

(Non-Patent Document 2) Tang, Libin, et al. "Deep ultraviolet photoluminescence of water-soluble self-passivated graphene quantum dots." ACS nano 6.6 (2012): 5102-5110.

(Non-Patent Document 3) Wu, Xu, et al. "Fabrication of highly fluorescent graphene quantum dots using L-glutamic acid for in vitro/in vivo imaging and sensing." Journal of Materials Chemistry C 1.31 (2013): 4676-4684.

SUMMARY

The present disclosure is directed to providing a method for producing carbon quantum dots including a process of bottom-up mode and providing high productivity.

The present disclosure is also directed to providing carbon quantum dots which use a nitrogen-containing organic precursor and contain about 3-10 wt % of nitrogen without introduction of any additional purification and doping processes, so that they are easily engineered in band-gap and show excellent electroconductivity and thermal safety.

In one aspect, there are provided nitrogen-doped carbon quantum dots as pyrolysis product of fumaronitrile.

According to an embodiment, the carbon quantum dots may be porous carbon quantum dots.

According to another embodiment, nitrogen may be doped in an amount of 3-10 wt % based on the total weight of the carbon quantum dots.

According to still another embodiment, the carbon quantum dots may have a thickness of 0.5-5 nm.

According to still another embodiment, the carbon quantum dots may have a ratio of sp2:sp3 ranging from 2.3:1 to 5.1:1.

According to yet another embodiment, the carbon quantum dots may be represented by the following Chemical Formula 1:

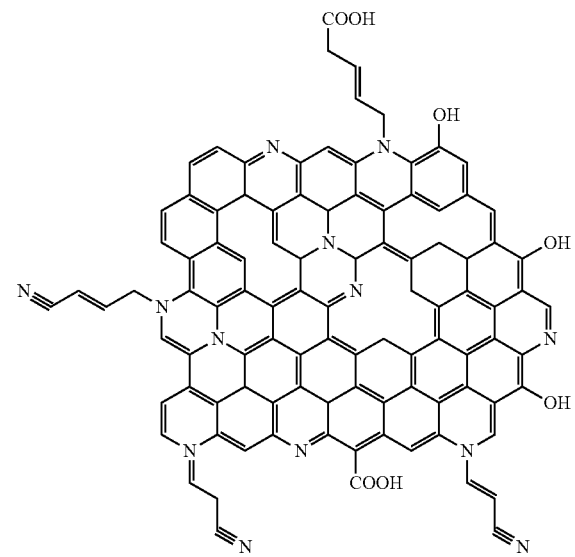

[Chemical Formula 1]

In another aspect, there is provided a method for producing carbon quantum dots, including: mixing fumaronitrile with a solvent in a reaction container; and carrying out pyrolysis of fumaronitrile to form carbon quantum dots.

According to an embodiment, fumaronitrile may be mixed with the solvent so that it may be dissolved in the solvent, wherein fumaronitrile may be used in an amount of 3-50 wt % based on the total weight of the solvent.

According to another embodiment, the solvent may include at least one selected from the group consisting distilled water, furane-based solvents and aldehyde-based solvents.

According to still another embodiment, the carbon quantum dots may be doped with nitrogen in a doping amount varied with the type of the solvent.

According to still another embodiment, the pyrolysis of fumaronitrile may be carried out at a temperature of 150-250° C.

According to yet another embodiment, the pyrolysis of fumaronitrile may be carried out for 5 minutes to 1 hour.

In still another aspect, there is provided an organic solar cell including an active layer containing the carbon quantum dots.

According to an embodiment, the active layer may include the carbon quantum dots in an amount of 0.2-5 wt % based on the weight of the active layer.

According to another embodiment, the organic solar cell may have a photoelectric conversion efficiency of 7.3%-8.6%. In yet another aspect, there is provided a photocatalyst including the carbon quantum dots.

According to the method for producing carbon quantum dots disclosed herein, it is possible to obtain a large amount of carbon quantum dots with high efficiency.

In addition, the high-quality carbon quantum dots obtained by the method disclosed herein use no oxidizing agent and reducing agent, which, otherwise are used for the conventional methods, provide an acidity of solution close to a neutral solution before and after the reaction to avoid a need for purification and separation processes, and thus requires a simplified process and reduces processing cost.

In addition, the method disclosed herein produces carbon quantum dots through decomposition of organic materials in a bottom-up mode, and thus allows production of carbon quantum dots with uniform quality through a single-step reaction, unlike the methods including crushing and dispersing a bulk carbonaceous material in a top-down mode.

The carbon quantum dots disclosed herein may be doped with 3-10 wt % of nitrogen without a need for a separate doping process. Thus, it is possible for the carbon quantum dots to show excellent electroconductivity and thermal safety.

Further, the photocatalyst including the carbon quantum dots disclosed herein may show a photocatalytic activity improved by about 2-20 times as compared to the conventional photocatalysts. Thus, the photocatalyst disclosed herein may be used widely in various industrial fields.

BRIEF DESCRIPTION OF THE DRAWINGS

FIG. 5A and FIG. 5B show the spectra illustrating the optical properties of the carbon quantum dots obtained according to an embodiment of the present disclosure, wherein FIG. 5A shows the photoluminescence excitation spectrum of the carbon quantum dots and FIG. 5B shows the photoluminescence spectrum.

DETAILED DESCRIPTION

Figure 1:
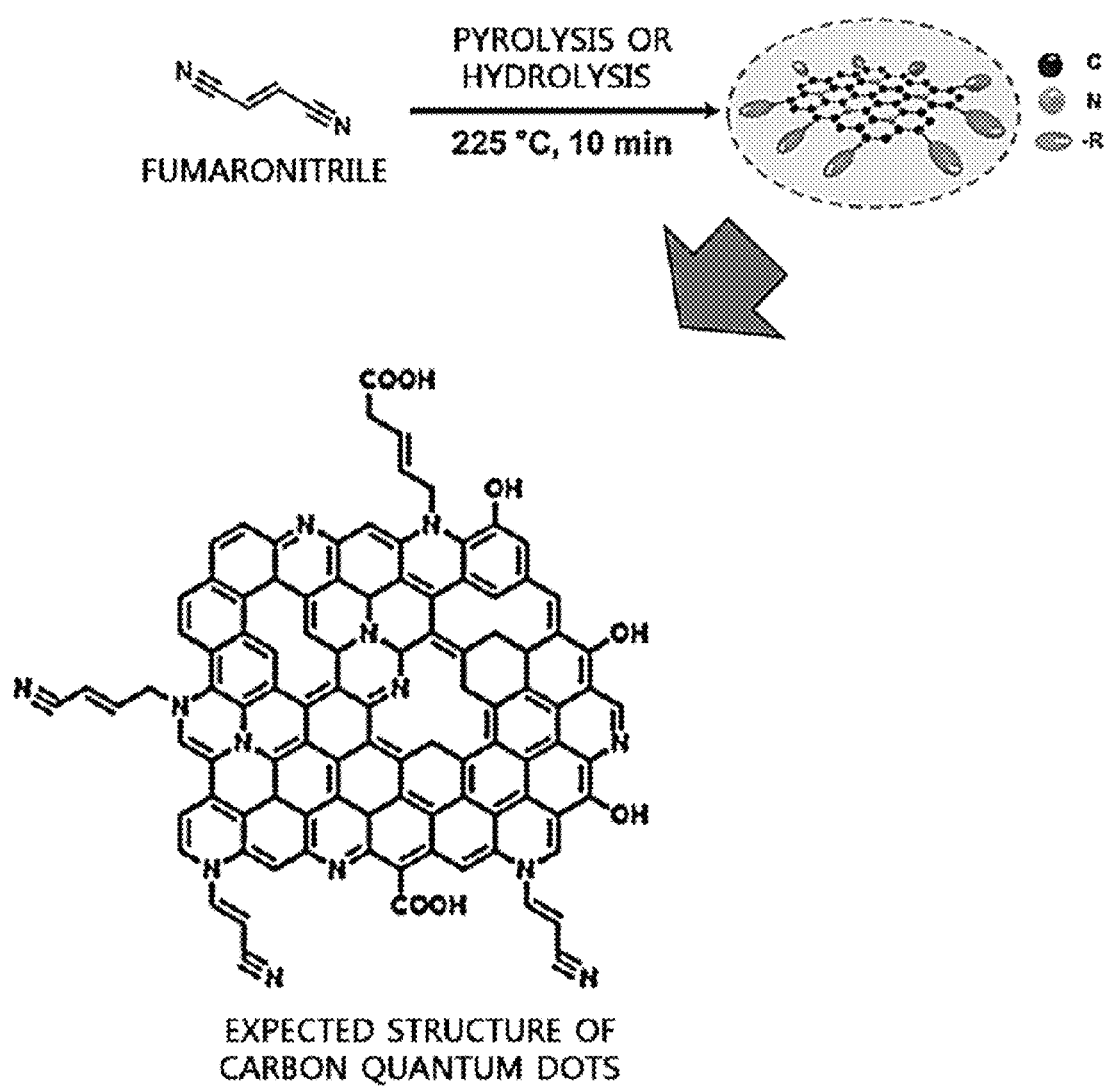
FIG. 1 is a schematic view illustrating the method for producing carbon quantum dots according to an embodiment.

As used herein, the term 'carbon quantum dots' means carbonaceous materials having a size of 20 nm or less.

Exemplary embodiments now will be described more fully hereinafter with reference to the accompanying drawings, in which exemplary embodiments are shown. The present disclosure may, however, be embodied in many different forms and should not be construed as limited to the exemplary embodiments set forth therein.

In one aspect, there is provided a method for producing carbon quantum dots, including: mixing fumaronitrile with a solvent in a reaction container; and carrying out pyrolysis of fumaronitrile to form carbon quantum dots.

The method for producing carbon quantum dots disclosed herein uses no oxidizing agent and reducing agent, which, otherwise, are used for the conventional processes, and provides an acidity of solution close to a neutral solution before and after the reaction to avoid a need for purification and separation processes, and thus requires a simplified process and reduces processing cost.

In addition, the method disclosed herein produces carbon quantum dots through decomposition of organic materials in a bottom-up mode, and thus allows production of carbon quantum dots with uniform quality through a single-step reaction, unlike the methods including crushing and dispersing a bulk carbonaceous material in a top-down mode.

Hereinafter, the method will be explained in more detail.

First, a nitrogen-containing highly crystalline nitrile-based material is mixed with a solvent in a reaction container.

According to an embodiment, among the nitrile-based materials, fumaronitrile precursor is used. As described hereinafter, the optical and electrical properties of carbon quantum dots may be varied with the type of precursor.

According to another embodiment, as fumaronitrile is mixed with the solvent, fumaronitrile may be dissolved into the solvent.

According to still another embodiment, fumaronitrile may be dissolved in the solvent in an amount up to 3-50 wt % based on the total weight of the solvent. When fumaronitrile is dissolved in an amount larger than 50 wt %, agglomeration of carbon quantum dots may occur.

Then, fumaronitrile is subjected to pyrolysis to obtain a plurality of carbon quantum dots.

Particularly, the pyrolysis of fumaronitrile may be carried out at a temperature of 150-250° C. for 10-20 minutes.

When the pyrolysis temperature is lower than 150° C., it is not possible to carry out pyrolysis sufficiently. When the pyrolysis temperature is higher than 250° C., it is not easy to control the size of carbon quantum dots. Particularly, since fumaronitrile has double and triple bonds therein, it is possible to obtain highly crystalline carbon quantum dots even at a low reaction temperature of 200° C. or less.

According to still another embodiment, when the pyrolysis is carried out for a time less than 5 minutes, a part of the precursor may not participate in the reaction. When the pyrolysis is carried out for a time more than 1 hour, carbon structures having a size of 20 nm or more may be formed.

According to still another embodiment, a plurality of fumaronitrile molecules may be pyrolyzed and decomposed so that they may be bound to each other, thereby forming a plurality of carbon quantum dots.

Then, after the solvent in which the carbon quantum dots are dispersed is removed, the carbon quantum dots may be freeze-dried to obtain carbon quantum dot powder.

According to still another embodiment, the freeze-drying may be carried out at a temperature ranging from −70° C. to −55° C.

In this manner, nitrogen-doped carbon quantum dots may be obtained as pyrolysis product of fumaronitrile.

According to still another embodiment, since fumaronitrile contains nitrogen, the carbon quantum dots may be formed while they are doped with nitrogen during the pyrolysis.

According to yet another embodiment, the carbon quantum dots may be doped with 3-10 wt % of nitrogen based on the total weight of the carbon quantum dots, depending on the type of solvent. In the case of a solvent having high reactivity to nitrile groups, the carbon quantum dots may be doped with nitrogen in an amount less than 3 wt %. In the case of a solvent having low reactivity, the carbon quantum dots may be doped with nitrogen in an amount larger than 10 wt %.

Meanwhile, the carbon quantum dots may have a thickness of 0.5-5 nm, specifically 1-1.5 nm.

According to an embodiment, the carbon quantum dots may have a number of layers between 1 and 3.

According to another embodiment, the carbon quantum dots may be porous carbon quantum dots.

In addition, the carbon quantum dots may have a high sp2:sp3 ratio, particularly a ratio of sp2:sp3 ranging from 2.3:1 to 5.1:1.

According to still another embodiment, the carbon quantum dots may be represented by the following Chemical Formula 1, but are not limited thereto:

[Chemical Formula 1]

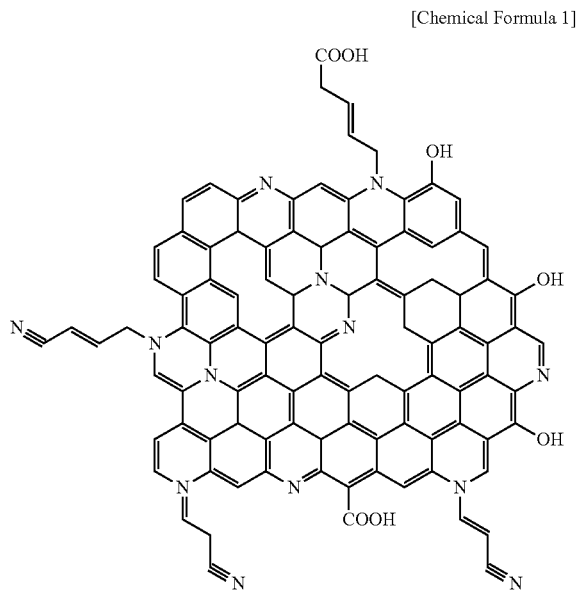

The carbon quantum dots may have excellent luminescence properties and high crystallinity. In addition, since the carbon quantum dots are doped with nitrogen, they may show excellent band-gap properties, when used as semiconductor material.

In another aspect, there is provided an organic solar cell including an active layer containing the carbon quantum dots.

According to an embodiment, the organic solar cell may include a first electrode, a first buffer layer, an active layer, a second buffer layer and a second electrode, stacked successively.

According to another embodiment, the first electrode may be an anode and the first electrode may be a transparent electrode.

According to still another embodiment, the transparent electrode may include a transparent and highly conductive material, but is not limited thereto. The first electrode may include a metal such as vanadium, chrome, copper, zinc or gold, or an alloy thereof; a metal oxide, such as zinc oxide, indium oxide, indium tin oxide (ITO) or indium zinc oxide (IZO); a combination of metal with oxide, such as ZnO:Al or SnO$_2$:Sb; a conductive polymer, such as poly(3-methylthiophene), poly[3,4-(ethylene-1,2-dioxy)thiophene] (PEDOT), polypyrrole and polyaniline, but is not limited thereto.

According to still another embodiment, the transparent electrode may further include a metal oxide/metal/metal oxide, such as MoO$_3$/Ag/MoO$_3$, graphene, carbon nanotubes, metal nanoparticles and metal wires, metal mesh, or a combination thereof.

According to still another embodiment, the transparent electrode may be a transparent conductive oxide layer. Particularly, the transparent conductive oxide layer may include, in addition to a glass or quartz plate, a flexible transparent substrate on which a conductive material is doped, such as plastic including polyethylene terephthalate (PET), polyethylene naphthalate (PEN), polypropylene (PP), polyimide (PI), polycarbornate (PC), polystyrene (PS), polyoxyethylene (POM), acrylonitrile styrene copolymer (AS resin), acrylonitrile butadiene styrene copolymer (ABS resin), triacetyl cellulose (TAC) and polyarylate (PAR), or the like. More particularly, the transparent conductive oxide layer may include indium tin oxide (ITO), fluorine doped tin oxide (FTO), aluminum doped zinc oxide (AZO), indium zinc oxide (IZO), $ZnO-Ga_2O_3$, $ZnO-Al_2O_3$ and antimony tin oxide (ATO), or the like, and more particularly ITO.

Meanwhile, the first buffer layer functions to reduce the work function of the first electrode, and may be formed, for example, by depositing polyethyleneimine ethoxylated (PEIE) through spin coating.

According to still another embodiment, the active layer may include an electron-donating material and an electron-accepting material as photoactive materials. Particularly, the active layer may include the nitrogen-doped carbon quantum dots as pyrolysis product of fumaronitrile.

Particularly, in the active layer, the electron-donating material forms exciton through an electron-hole pair under light excitation, and the exciton are separated into an electron and hole at the electron donator/electron acceptor interface. The separated electron and hole are transported to the electron-donating material and electron-accepting material, respectively, and then are collected at the first electrode and the second electrode, respectively, so that they may be utilized as electric energy in the exterior part.

According to still another embodiment, the active layer may include the carbon quantum dots in an amount of 0.2-5 wt %, particularly 1-2 wt %.

According to still another embodiment, the organic solar cell may further include a second buffer layer of the second electrode, disposed between the active layer and the second electrode. Particularly, according to still another embodiment, the second buffer layer of the second electrode may be disposed between the second electrode and the active layer, and the second buffer layer may control the interfacial energy between the second electrode and the active layer to induce smooth flow of electrons.

According to still another embodiment, the second buffer layer may include a conductive polymer and/or metal oxide. Particularly, the conductive polymer may be a conjugated polymer material, dielectric polymer, graphene, carbon nanotubes, or a combination thereof. The conjugated polymer material may include poly[(9,9-bis(30-(N,N-dimethyl-amino)propyl)-2,7-fluorene)-alt-2,7-(9,9-dioctylfluorene)] (PEN), poly[9,9'-bis[6"-(N,N,N-trimethylammonium) hexyl]fluorene-co-alt-phenylene] dibromide (FPQ-Br), or the like. In addition, the dielectric polymer may be polyethylenimine (PEI) and polyethylenimine ethoxylated (PEIE). Further, the conductive polymer may include at least one selected from the group consisting of phthalocyanine derivatives, naphthalocyanine derivatives, aromatic amine compounds, polyethylene dioxythiophene (PEDOT:PSS) and polyaniline.

In addition, the metal oxide contained in the second buffer layer of the second electrode may include $V_2O_5$ and/or $MoO_3$.

According to still another embodiment, the second electrode may function as cathode, and the second electrode may be a metal electrode, etc.

According to still another embodiment, the metal electrode may include a metal having a small work function, but is not limited thereto. Particularly, the metal electrode may be a metal, such as magnesium, calcium, sodium, potassium, titanium, indium, yttrium, lithium, gadolinium, aluminum, silver, tin and lead, or an alloy thereof; a multi-layer material, such as LiF/Al, $LiO_2$/Al, LiF/Fe, Al:Li, Al:$BaF_2$, or Al:$BaF_2$:Ba, but is not limited thereto. Particularly, according to still another embodiment, the metal electrode may include at least one selected from the group consisting of silver (Ag), aluminum (Al), platinum (Pt), tungsten (W), copper (Cu), molybdenum (Mo), gold (Au), nickel (Ni) and palladium (Pd). More particularly, the metal electrode may be silver (Ag).

As mentioned above, the organic solar cell includes the nitrogen-doped carbon quantum dots in its active layer.

The carbon quantum dots may have excellent luminescence properties and high crystallinity. In addition, since the carbon quantum dots are doped with nitrogen, they may show excellent band-gap properties when used as semiconductor material. Thus, the organic solar cell may provide excellent photoelectric force and photoelectric conversion efficiency.

According to yet another embodiment, the organic solar cell may show a photoelectric conversion efficiency of 7.3%-8.6%.

In still another aspect, there is provided a photocatalyst including the carbon quantum dots.

According to an embodiment, the photocatalyst may include titanium dioxide powder and the carbon quantum dots may be present in an amount of 0.5-30 wt % based on the total weight of the titanium dioxide powder. When the carbon quantum dots are present in an amount less than 0.5 wt %, the activity of the photocatalyst may be degraded in the visible light region. When the carbon quantum dots are present in an amount larger than 30 wt %, the solubility may be degraded.

According to another embodiment, the photocatalyst may show a photocatalytic activity improved by about 2-20 times as compared to the conventional photocatalysts. It is thought that such a result is derived from the p type and n type domains formed in a plural number in the carbon quantum dots and affecting a degree of generation of free radicals required for a photocatalyst-based photolysis reaction.

While the exemplary embodiments have been shown and described, it will be understood by those skilled in the art that various changes in form and details may be made thereto without departing from the spirit and scope of the present disclosure as defined by the appended claims. In addition, many modifications can be made to adapt a particular situation or material to the teachings of the present disclosure without departing from the essential scope thereof. Therefore, it is intended that the present disclosure will include all embodiments falling within the scope of the appended claims.

The examples and experiments will now be described. The following examples and experiments are for illustrative purposes only and not intended to limit the scope of the present disclosure.

Example 1

First, an aqueous solution containing 200 mg of fumaronitrile dispersed in 50 mL of distilled water is introduced to a 100 mL round-bottom flask and heated in an oil bath equipped with a reflux condenser at 220° C. for 25 minutes to decompose and crystallize fumaronitrile, an organic precursor, in aqueous solution, thereby providing a plurality of carbon quantum dots. Then, a vacuum rotary concentrator is used to remove distilled water completely in the aqueous solution including the carbon quantum dots and the carbon quantum dots are freeze dried at −70° C. to obtain yellow colored carbon quantum dot powder.

Examples 2-4

Example 1 is repeated, except that THF, butyl aldehyde or benzyl aldehyde is used instead of distilled water, thereby providing carbon quantum dot powder according to each of Examples 2-4.

Example 5

The carbon quantum dots obtained according to Example 1 are added to an active layer in an amount of 2 wt % based on the total weight of the active layer to provide an active layer. Then, the active layer is used to provide an organic solar cell device having a structure of ITO/PEIE/PTB7:PC$_{71}$BM (+2 wt % N-CQDs)/MoO$_3$/Ag.

Examples 6-9

To 10 mL of each of the aqueous solutions of carbon quantum dots according to Example 1-4 (concentration: 0.01 mg/mL), 20 mg of a titanium dioxide (TiO$_2$) support is dissolved and the resultant solution is agitated at 70° C. under 100 rpm for 8 hours. After the completion of the reaction, a rotary vacuum evaporator is used to remove distilled water and a drying process is carried out to recover the resultant photocatalyst material (Example 6: TiO$_2$@NG_DW, Example 7: TiO$_2$@NG_THF, Example 8: TiO$_2$@NG_Bu, Example 9: TiO$_2$@NG_Be).

Comparative Example 1

Example 5 is repeated to obtain an active layer under the same conditions, except that no carbon quantum dots are added to the active layer. The active layer is used to provide an organic solar cell device having a structure of ITO/PEIE/PTB7:PC$_{71}$BM/MoO$_3$/Ag.

Comparative Example 2

To carry out comparative evaluation for an organic material removal ratio (%) in water, pure titanium dioxide powder and photocatalyst materials according to Examples 6-9 (TiO$_2$@NG_DW, TiO$_2$@NG_THF, TiO$_2$@NG_Bu, TiO$_2$@NG_Be) are used as photocatalysts, after attaching a 400 nm cutoff filter to the light source of a 300 W xenon lamp. The test conditions are as follows: concentration of rhodamine B (RhB) 100 mg/L, pH 6.5±0.2, temperature 25° C., and total reaction time 40 minutes.

Test Example 1: Evaluation for Acidity

Figure 2A:
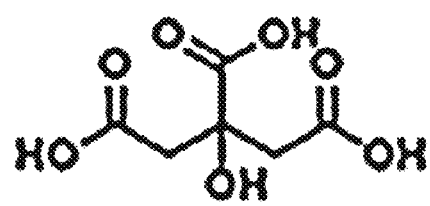
FIGS. 2A and 2B show the results of acidity measurement for the carbon quantum dot solutions obtained by the conventional method and the method according to an embodiment of the present disclosure.
Figure 2A:
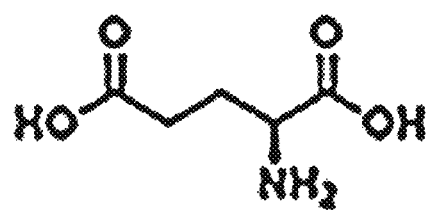
Figure 2A:
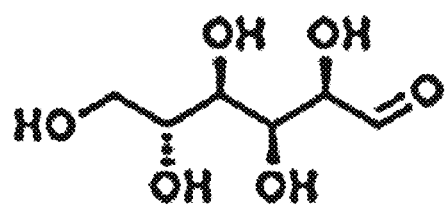
Figure 2A:
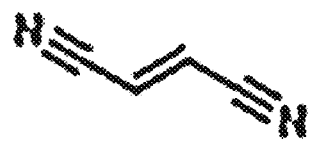
Figure 2B:
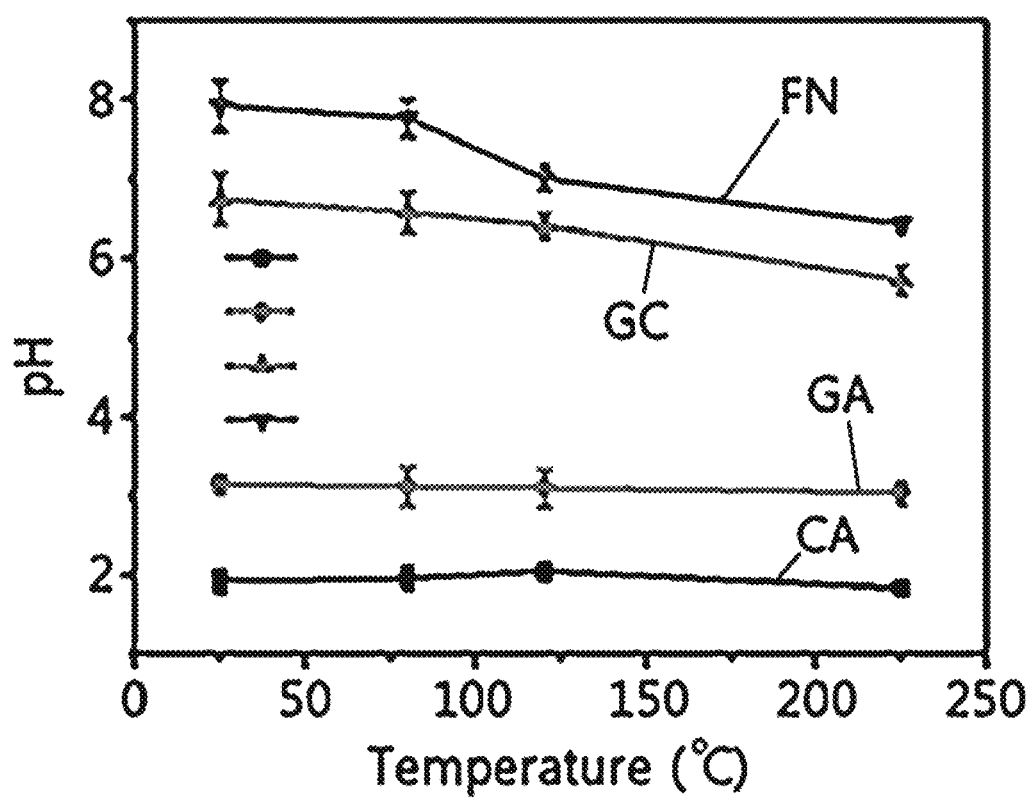

The carbon quantum dots obtained by using the conventional precursors and the carbon quantum dots obtained according to Example 1 are evaluated for acidity and the results are shown in FIGS. 2A and 2B. Referring to FIGS. 2A and 2B, it can be seen that when using the conventional precursors, glucose, citric acid or glutamic acid, the resultant carbon quantum dot solution is acidic. On the contrary, the carbon quantum dots according to Example 1 are nearly neutral. Therefore, the carbon quantum dots obtained according to an embodiment of the present disclosure require no purification and separation processes and are produced by a simplified process, thereby reducing the processing cost.

Test Example 2: Determination of Nanostructures

Figure 3:
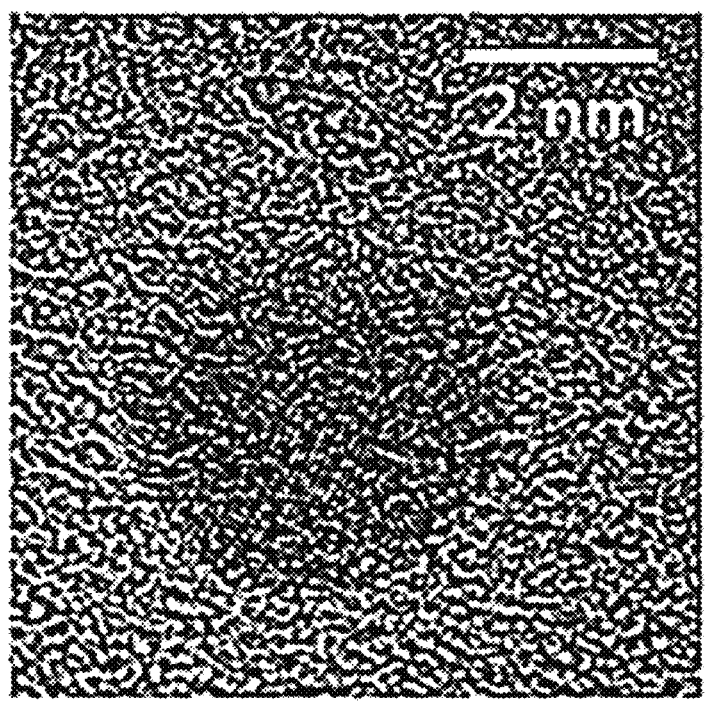
FIG. 3 is a transmission electron microscopic (TEM) image of the carbon quantum dots obtained according to an embodiment of the present disclosure.
Figure 4A:
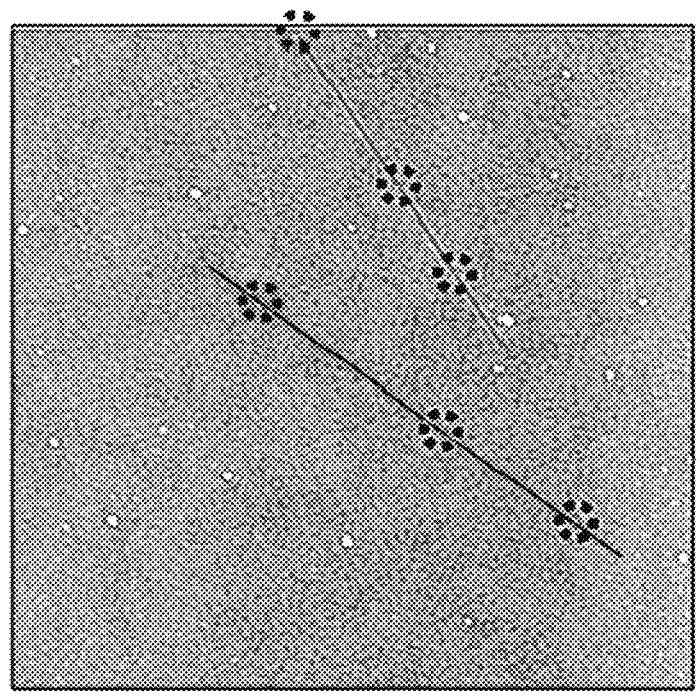
FIGS. 4A and 4B show an atomic force microscopic (AFM) image and a graph illustrating the thickness of the carbon quantum dots obtained according to an embodiment of the present disclosure, respectively.
Figure 4B:
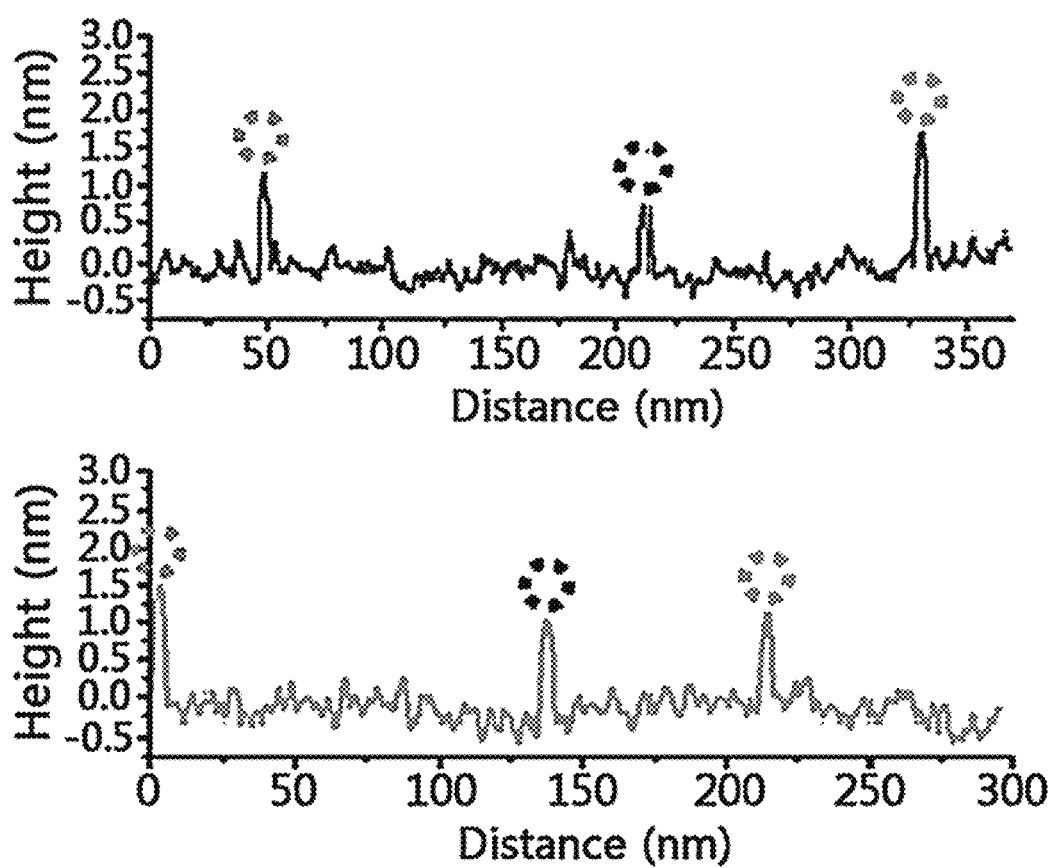

The structure of the carbon quantum dots according to Example 1 is determined through a transmission electron microscope and atomic force microscope, and the results are shown in FIG. 3 and FIGS. 4A and 4B.

FIG. 3 FIGS. 4A and 4B show a TEM image, an AFM image and a graph regarding the carbon quantum dots according to Example 1, respectively.

Referring to FIG. 3, it can be seen that highly crystalline carbon quantum dots are obtained even at a low reaction temperature of 220° C. or less. In addition, it can be seen from FIGS. 4A and 4B that the carbon quantum dots according to Example 1 have a thickness of about 1-1.5 nm, suggesting that carbon quantum dots having a small number of layers of 1-3 are produced well.

Test Example 3: Luminescence Properties

Figure 5A:
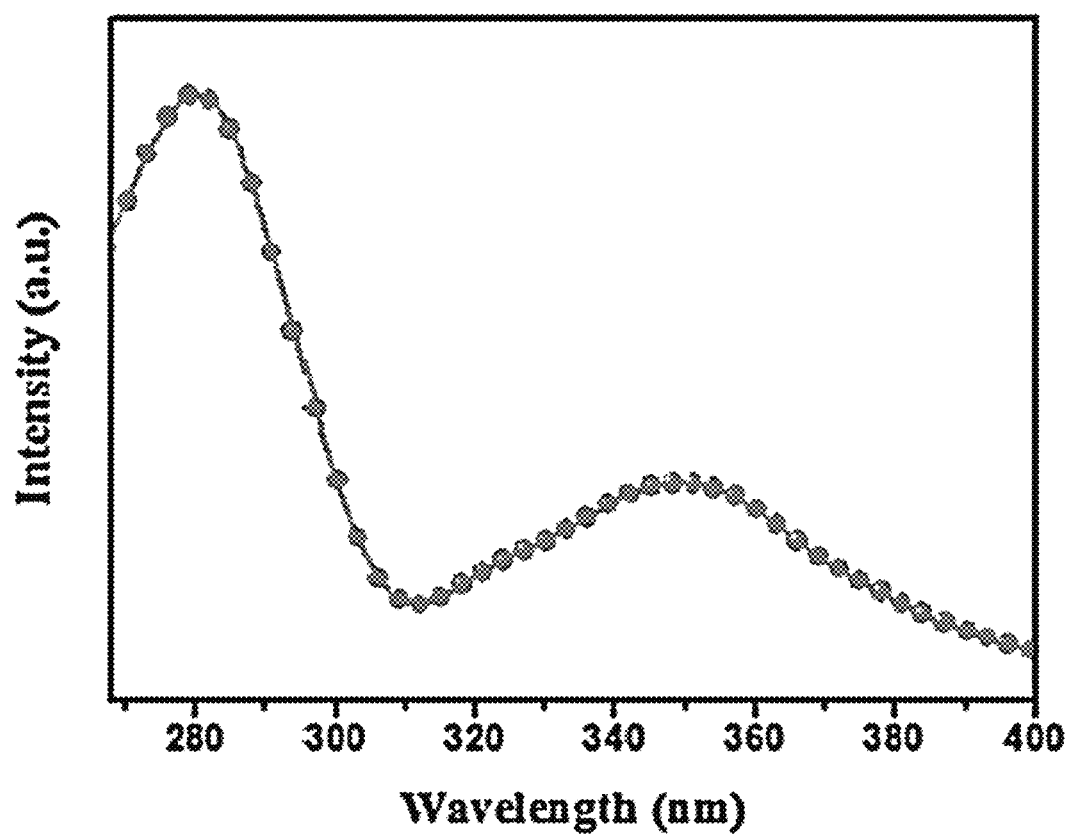
Figure 5B:
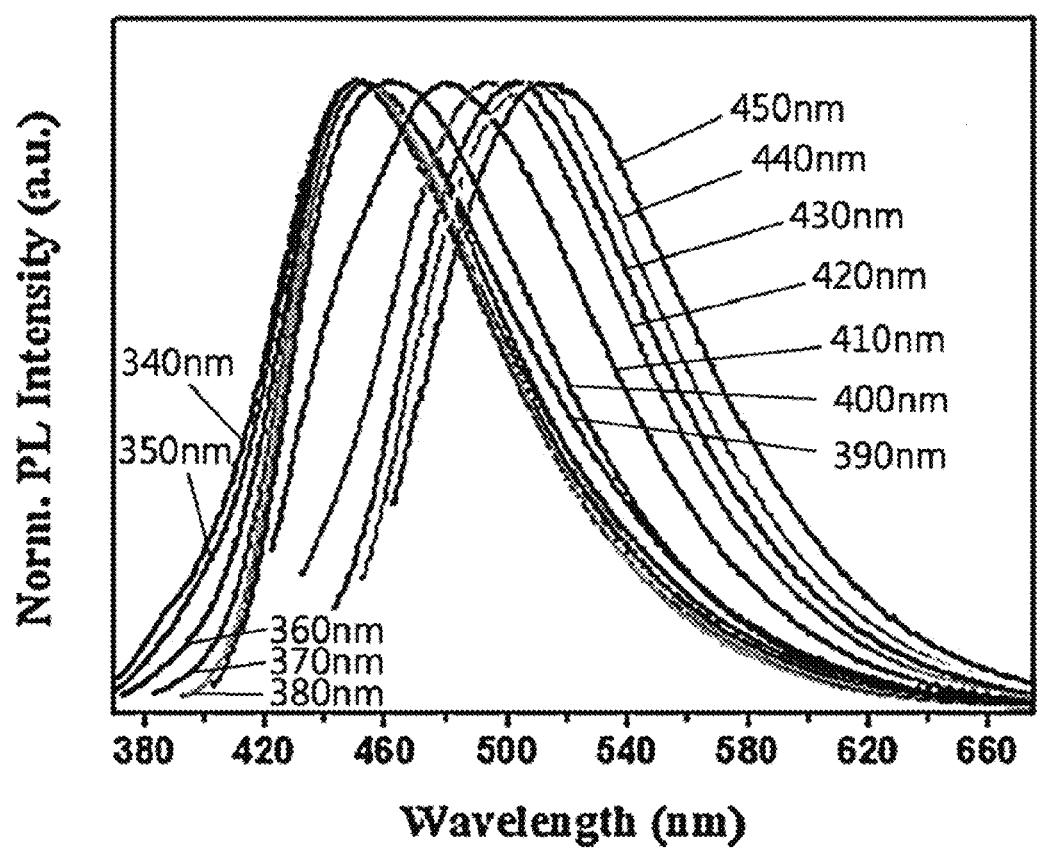

The carbon quantum dots according to Example 1 are determined for optical properties, and the results are shown in FIG. 5A and FIG. 5B.

FIG. 5A shows the photoluminescence excitation spectrum of the carbon quantum dots, and FIG. 5B shows the photoluminescence spectrum thereof. It can be seen from FIG. 5A that the carbon quantum dots according to Example 1 show strong photoluminescence properties at 280 nm and 350 nm. It can be seen from FIG. 5B that the carbon quantum dots according to Example 1 show strong photoluminescence properties at a wavelength of excitation light of 300-600 nm. This suggests that the carbon quantum dots have good photoluminescence properties.

Test Example 4: Determination of Structural Characteristics

Figure 6A:
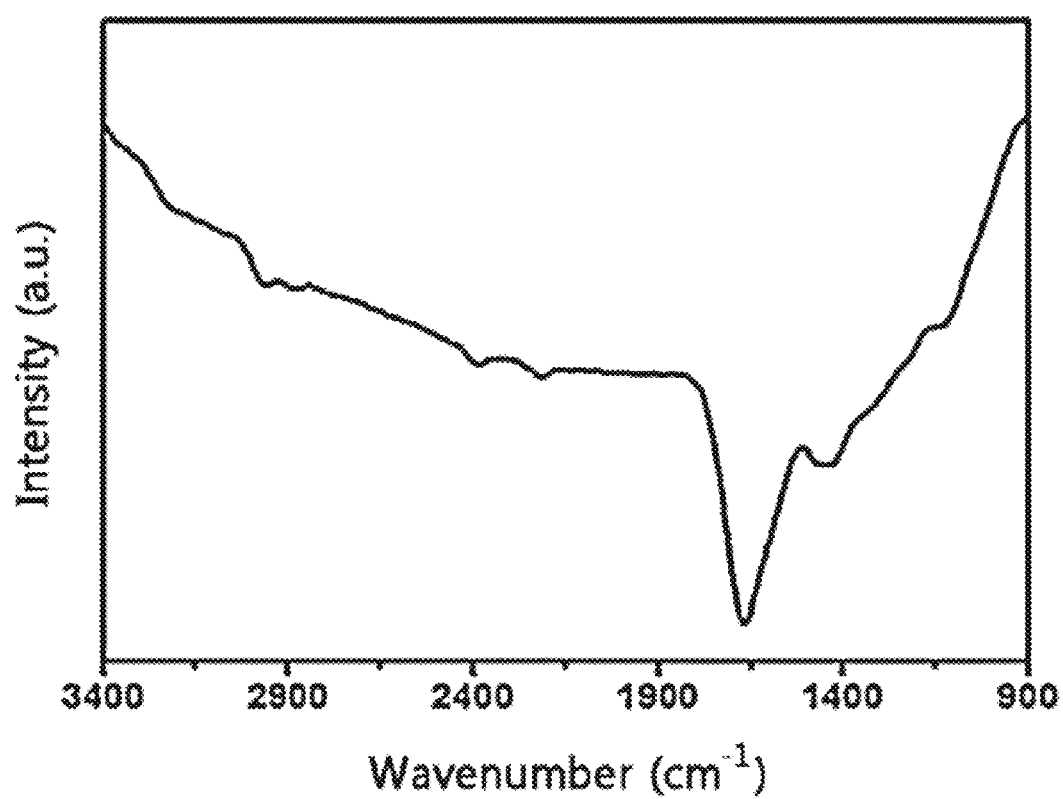
FIGS. 6A and 6B show the spectra determined by Fourier Transform Infrared (FT-IR) of the carbon quantum dots obtained according to an embodiment of the present disclosure.
Figure 6B:
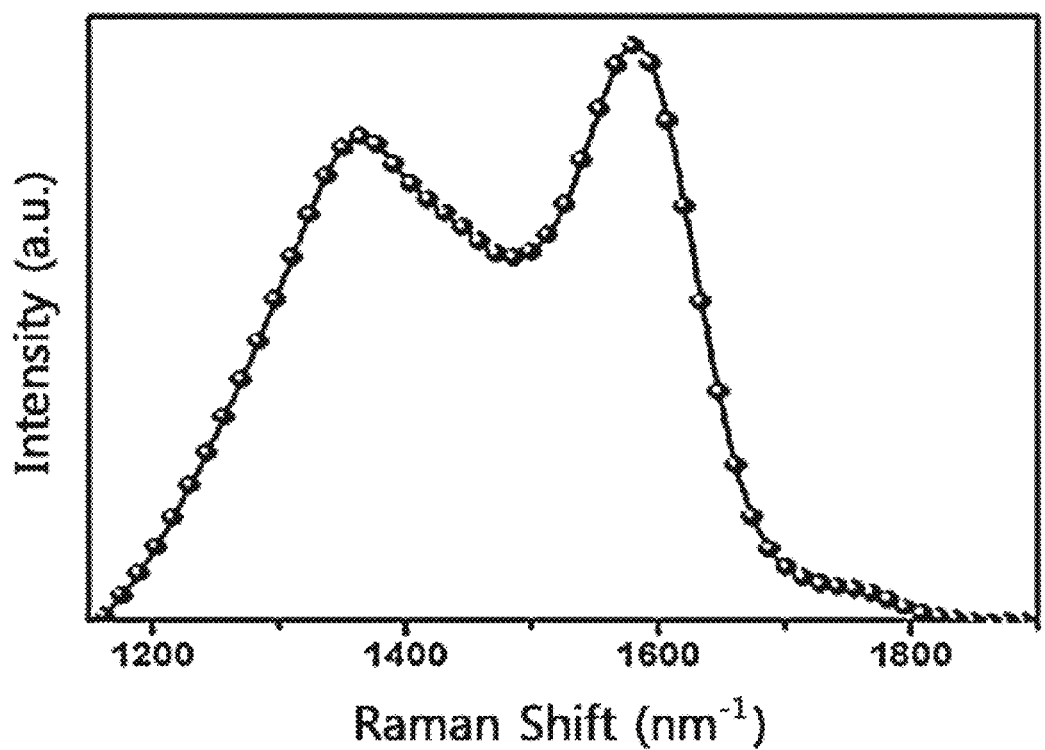

The carbon quantum dots according to Example 1 are analyzed by an infrared spectrometer and Raman spectrometer, and the results are shown in FIGS. 6A and 6B. In addition, the carbon quantum dots are analyzed by X-ray photoelectron spectroscopy (XPS) and the results are shown in FIGS. 7A and 7B.

Referring to FIG. 6A, the carbon quantum dots according to Example 1 show a small O—H absorption peak (3300-3400 cm$^{-1}$) corresponding to a degree of defects. This demonstrates that the carbon quantum dots disclosed herein have high quality and high crystallinity. Particularly, referring to FIG. 6B, G peak observed in the graphitic structure appears with high intensity at around 1580 cm$^{-1}$, suggesting that carbon quantum dots are produced well.

Figure 7A:
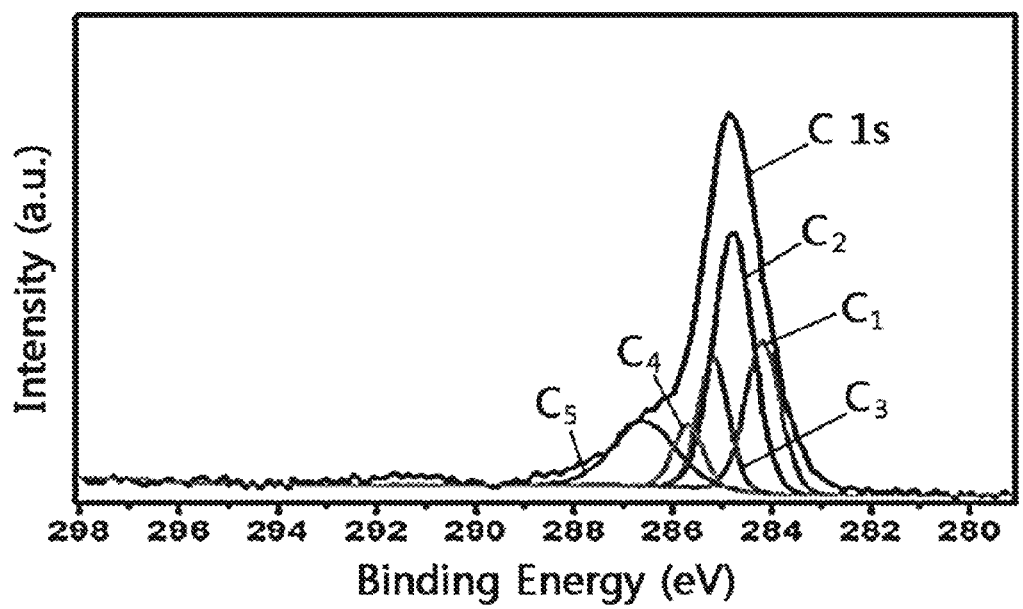
FIGS. 7A and 7B show the spectra determined by X-ray photoelectron spectroscopy of the carbon quantum dots obtained according to other embodiments of the present disclosure.
Figure 7B:
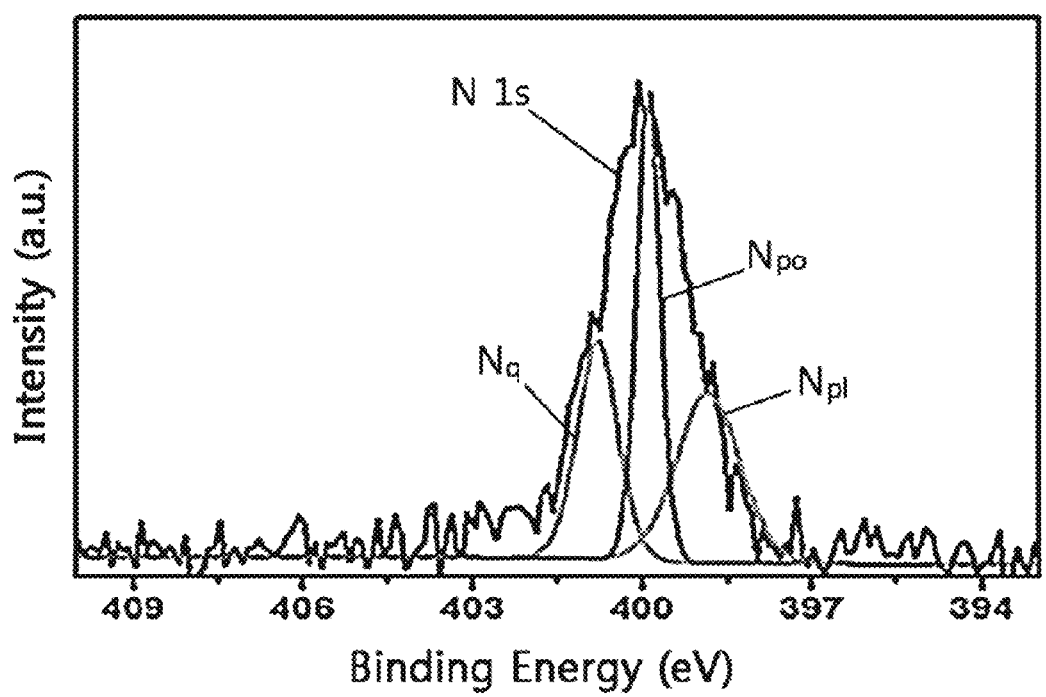

Meanwhile, referring to FIG. 7A, the carbon quantum dots according to Example 1 show the highest peak for C—C bonds and show small peaks for C—O and C=O bonds corresponding to defects. This demonstrates that the carbon quantum dots have high crystallinity. In addition, FIG. 7B shows a nitrogen bond spectrum and demonstrates the presence of nitrogen-based functional groups in the carbon quantum dots. Therefore, it can be seen that nitrogen-containing carbon quantum dots are produced through the above-described single step process.

Figure 8A:
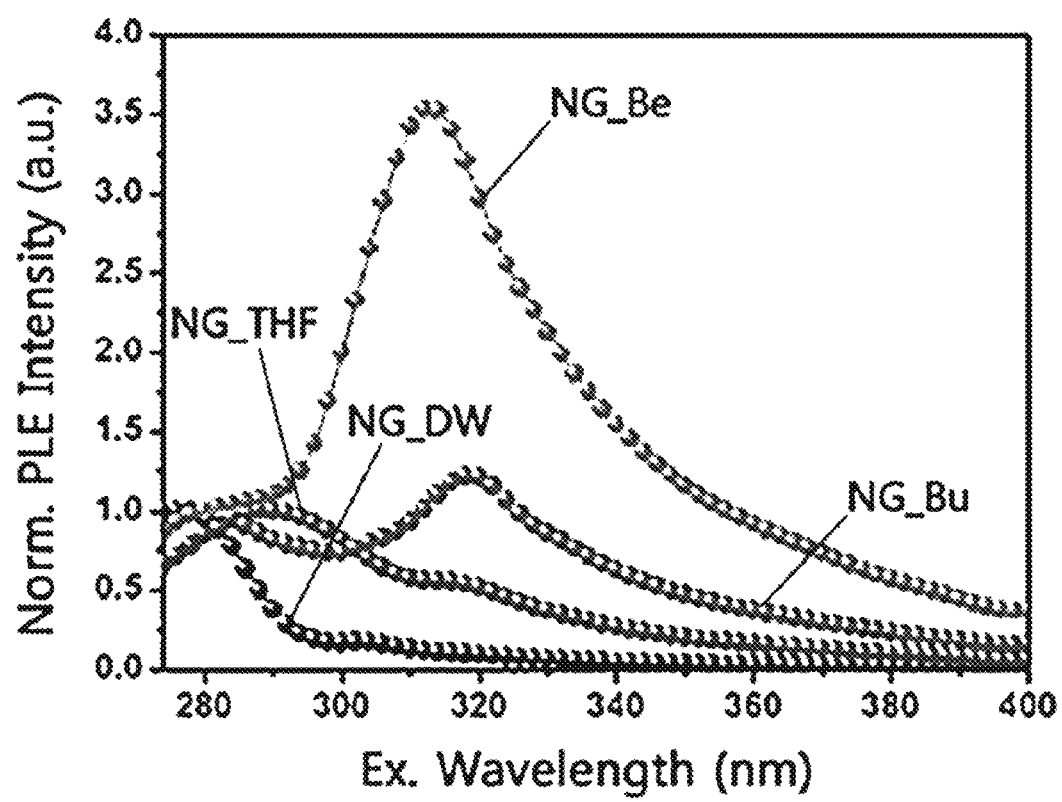
FIGS. 8A and 8B show the spectra illustrating the optical properties of the carbon quantum dots obtained according to other embodiments of the present disclosure.
Figure 8B:
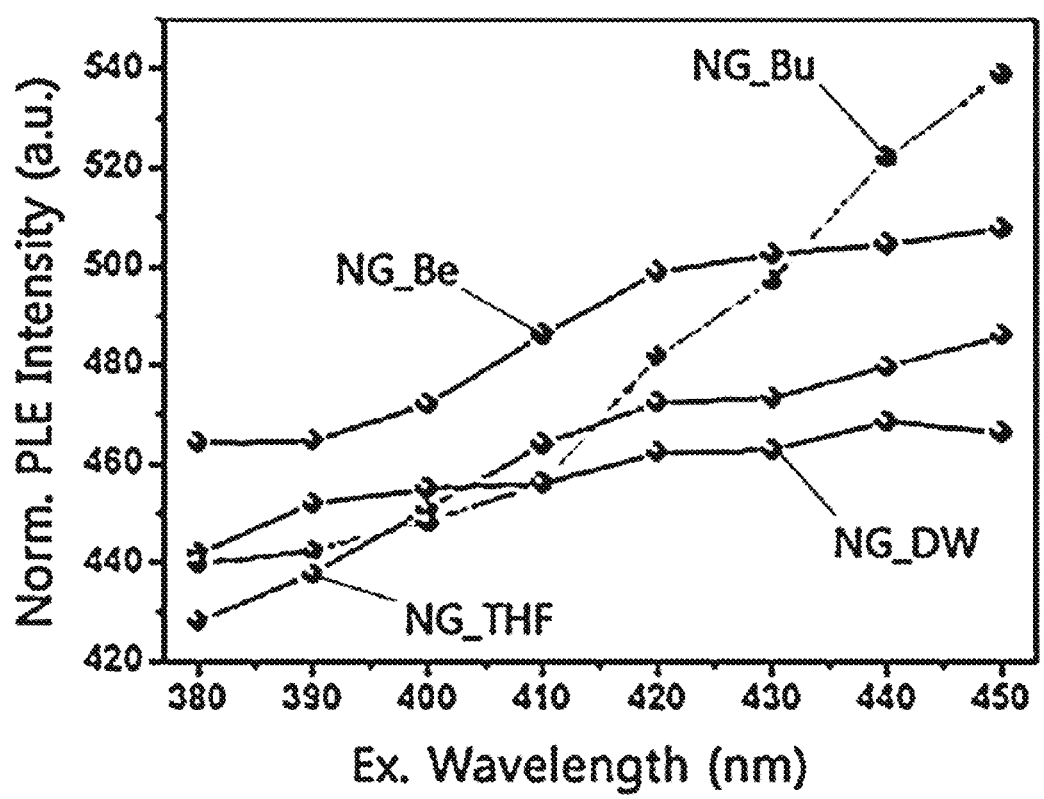
Figure 9A:
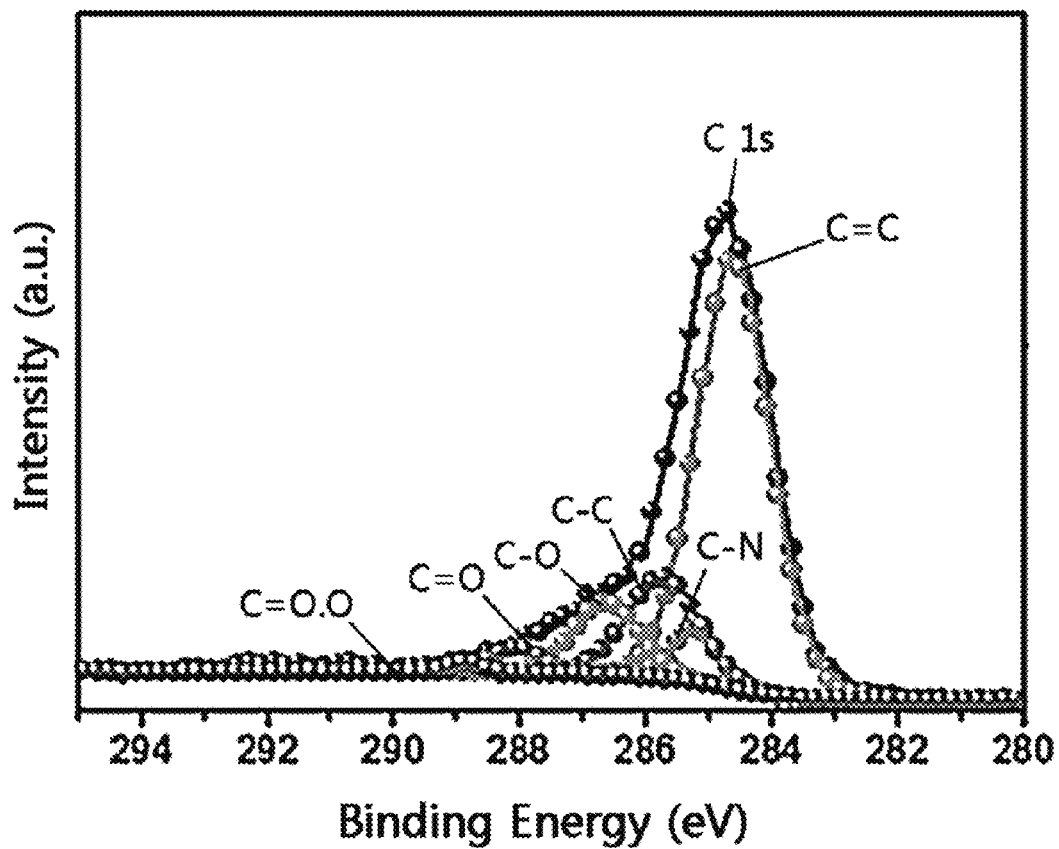
FIGS. 9A to 9D show the spectra determined by X-ray photoelectron spectroscopy of the carbon quantum dots obtained according to other embodiments of the present disclosure.
Figure 9B:
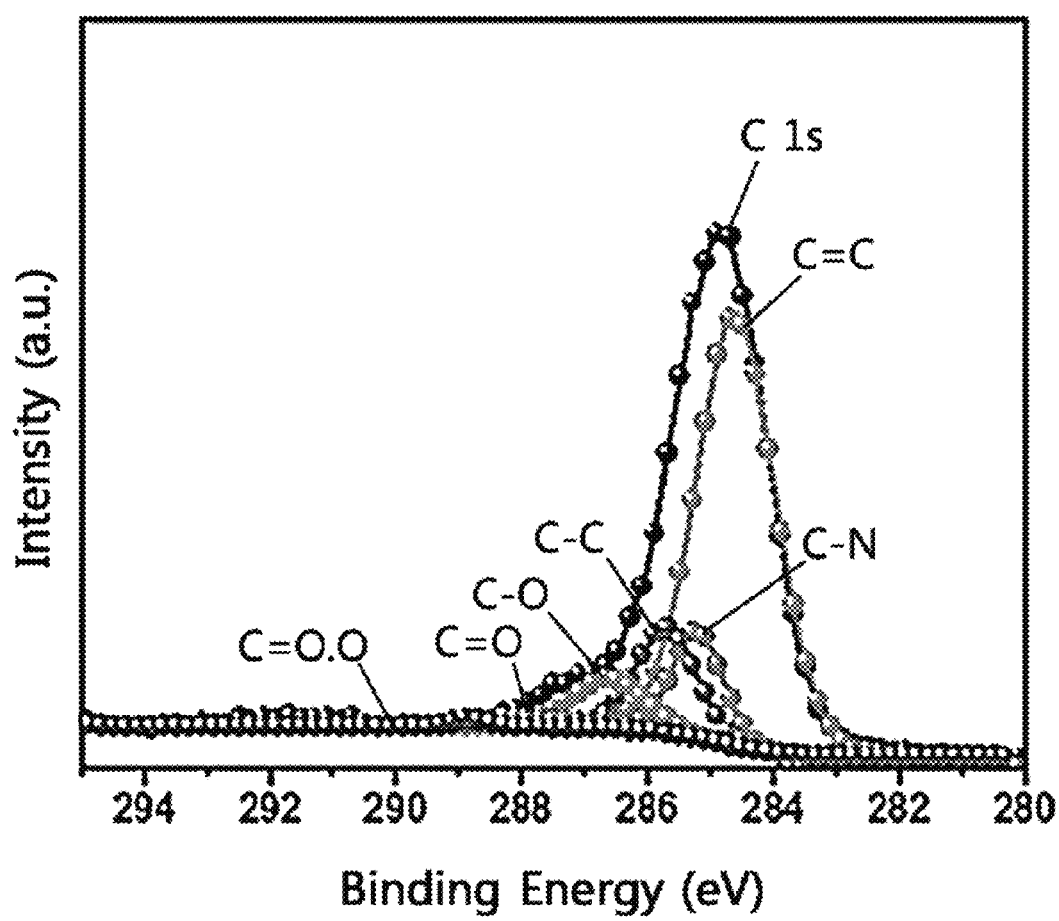
Figure 9C:
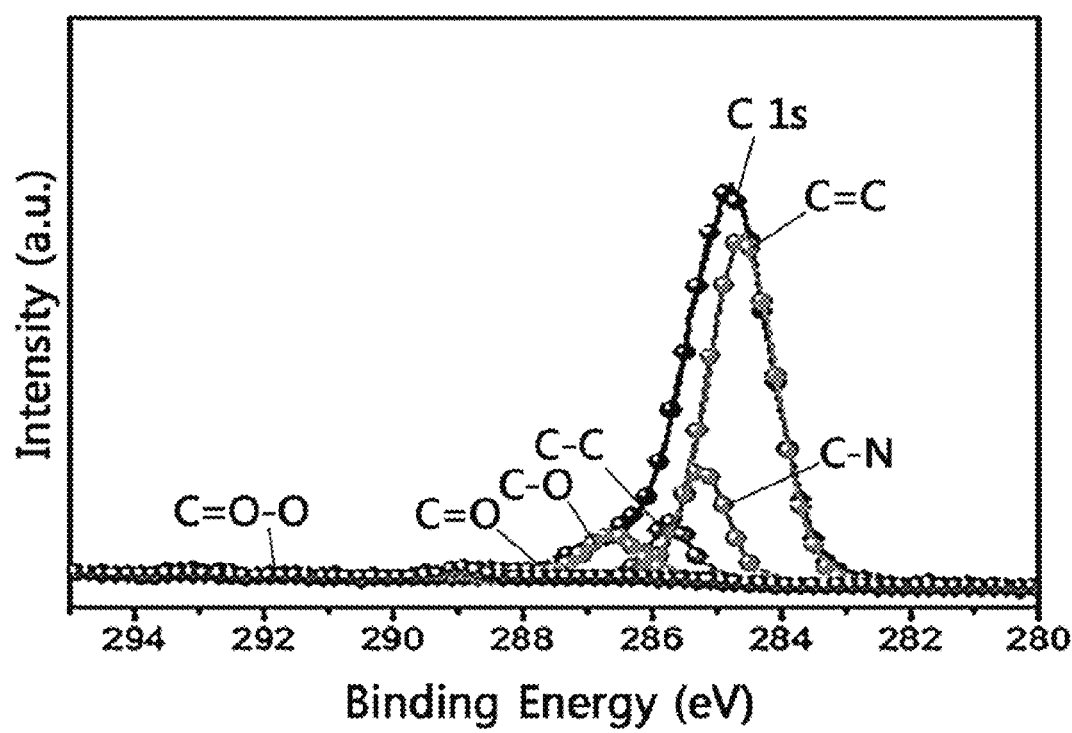
Figure 9D:
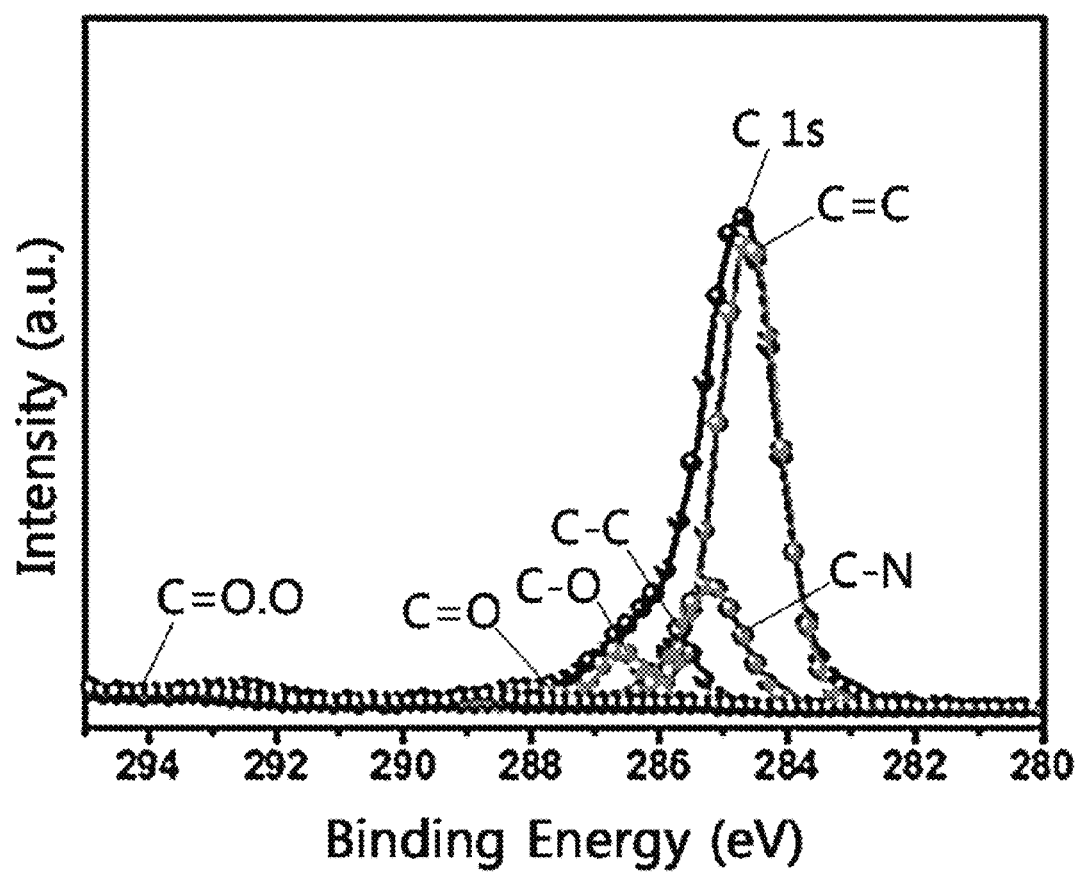

Test Example 5: Determination of Photoluminescence Properties and Structural Characteristics Depending on Type of Solvent The carbon quantum dots according to Examples 1-4 are determined for optical properties, and the results are shown in FIGS. 8A and 8B. Particularly, FIG. 8A shows the photoluminescence excitation spectrum of each of the carbon quantum dots according to Examples 1-4. FIG. 8B shows the absorption wavelength depending on photoexcitation wavelength. Referring to FIG. 8A, it can be seen that the carbon quantum dots according to Examples 1-4 show different photoluminescence excitation properties but generally show strong photoluminescence excitation properties at about 270-280 nm and 310-320 nm. It can be seen from FIG. 8B illustrating photoluminescence properties that different photoluminescence properties are realized depending on type of solvent used for the production of carbon quantum dots. Therefore, it can be seen that carbon quantum dots undergo a change in chemical structure depending on type of solvent used for the production thereof. Thus, it is possible to produce carbon quantum dots having various light absorption properties based on this. Referring to FIGS. 9A and 9B, it can be seen that the carbon quantum dots according to Example 1 show a relative small sp2:sp3 ratio by which the crystallinity can be evaluated indirectly and have a low amount of C—N bonds corresponding to a degree of doping with nitrogen atoms. However, the carbon quantum dots according to Example 1 have a relatively large amount of C—O and C═O bonds corresponding to defects. On the contrary, the carbon quantum dots obtained according to Example 4 show a relatively large sp2:sp3 ratio and have a relatively large amount of C—N bonds corresponding to a degree of doping with nitrogen atoms. However, the carbon quantum dots according to Example 4 have a relative small amount of C—O and C═O bonds corresponding to defects. Therefore, it can be seen that the carbon quantum dots have high crystallinity.

Figure 11:
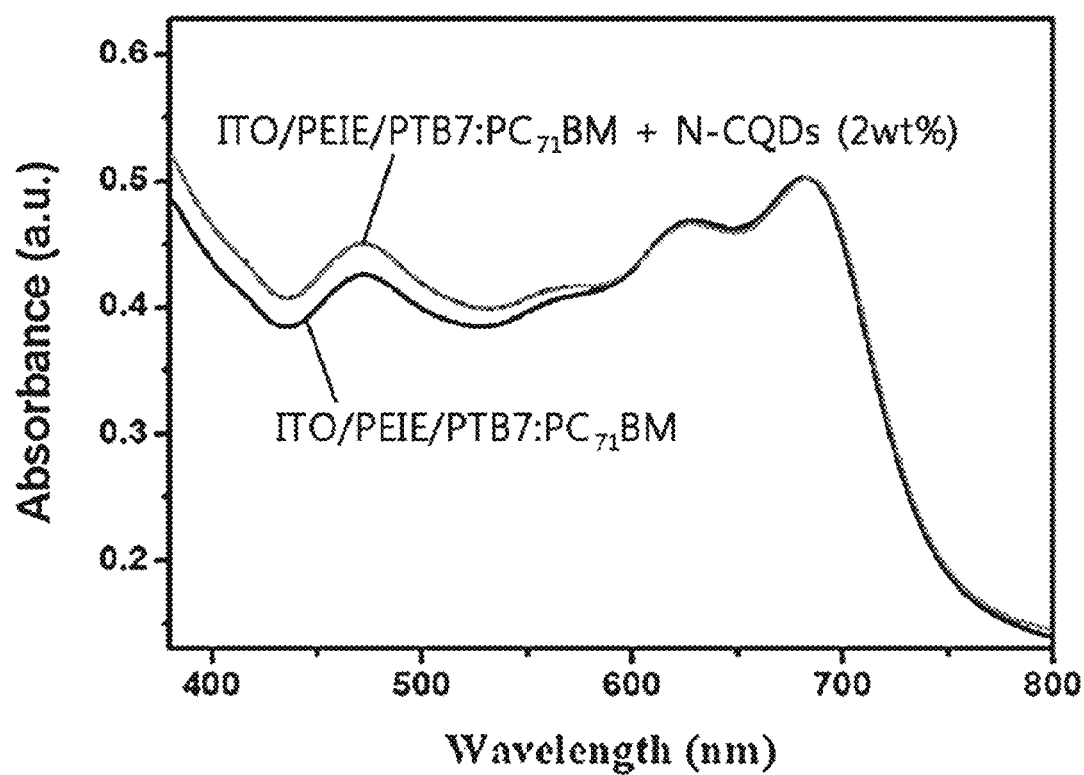
FIG. 11 shows the light absorption spectra of the organic solar cells according to Example 5 and Comparative Example 1.
Figure 12:
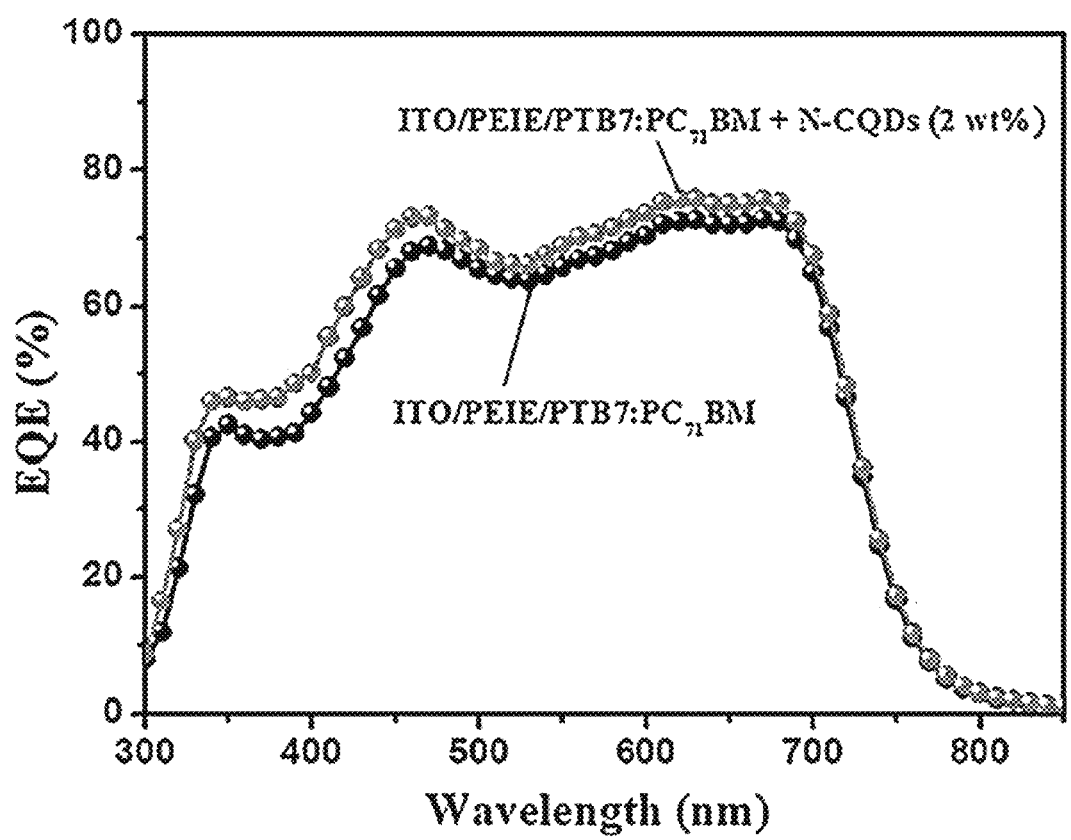
FIG. 12 is a graph illustrating the incident photo-to-current conversion efficiency (IPCE) of each of the organic solar cells according to Example 5 and Comparative Example 1.

Test Example 6: Photoelectric Force and Photoelectric Conversion Efficiency of Organic Solar Cells The organic solar cells according to Example 5 and Comparative Example 1 are determined for photoelectric force effect and photoelectric conversion efficiency, and the results are shown in FIG. 10-FIG. 12.

Figure 10:
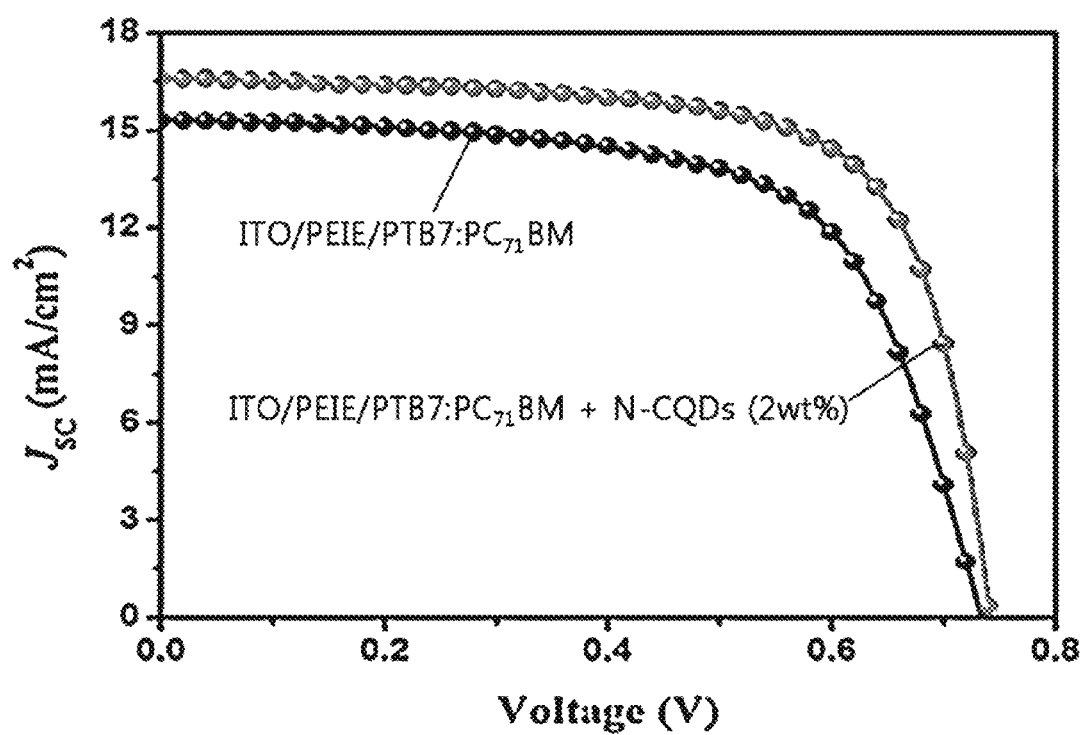
FIG. 10 is a graph illustrating the current density-voltage (J-V) properties of the organic solar cells according to Example 5 and Comparative Example 1.

FIG. 10 is a graph illustrating the current density-voltage (J-V) properties of the organic solar cells according to Example 5 and Comparative Example 1. FIG. 11 is a light absorption spectrum of the photoactive layer used for each of the organic solar cells according to Example 5 and Comparative Example 1.

Meanwhile, the following Table 1 shows the open circuit voltage ($V_{oc}$), short cut current density ($J_{sc}$), charging rate (FF) and photoelectric conversion efficiency (PCE) of each of the organic solar cells according to Example 5 and Comparative Example 1, as disclosed in FIG. 10.

Table 1

TABLE 1

| Composition of Active Layer | $J_{sc}$ (mA/cm$^2$) | $V_{oc}$ (V) | FF (%) | PCE (%) |
|---|---|---|---|---|
| PTB7:PC$_{71}$BM | 15.3 | 0.73 | 0.65 | 7.3 |
| PTB7:PC$_{71}$BM + 2 wt % N-CQDs | 16.6 | 0.74 | 0.71 | 8.6 |

Referring to FIG. 10-FIG. 12 and Table 1, as compared to the organic solar cell according to Comparative Example 1, it is possible to obtain an organic solar cell device having a photoelectric conversion efficiency improved by about 18%, when adding a small amount of carbon quantum dots to an active layer. Particularly, it can be seen that the organic solar cell according to Example 5 shows a significant increase in $J_{sc}$. It is thought that this is because N-CQDs mixed in the active layer in a small amount supplements the light absorption in a region with a relatively small wavelength (~450 nm) and thus increases production of free charges in the organic solar cell, so that $J_{sc}$ may be improved, as can be seen from FIG. 11.

Meanwhile, FIG. 12 is a graph illustrating the incident photo-to-current conversion efficiency (IPCE) of each of the organic solar cells according to Example 5 and Comparative Example 1 including an active layer to which 2 wt % of carbon quantum dots are added. It can be seen that this conforms to the graph of J-V characteristics as shown in FIG. 10. In the case of the organic solar cell using carbon quantum dots according to Example 5, it shows higher photoelectric conversion efficiency in a wavelength range of 300-800 nm, as compared to the organic solar cell device according to Comparative Example 1. It is thought that this is because the carbon quantum dots increases free charges and relatively improves the efficiency of charge transport to the electron-donating and electron-accepting materials forming the active layer.

Test Example 7: Determination of Photolysis Efficiency

Figure 13:
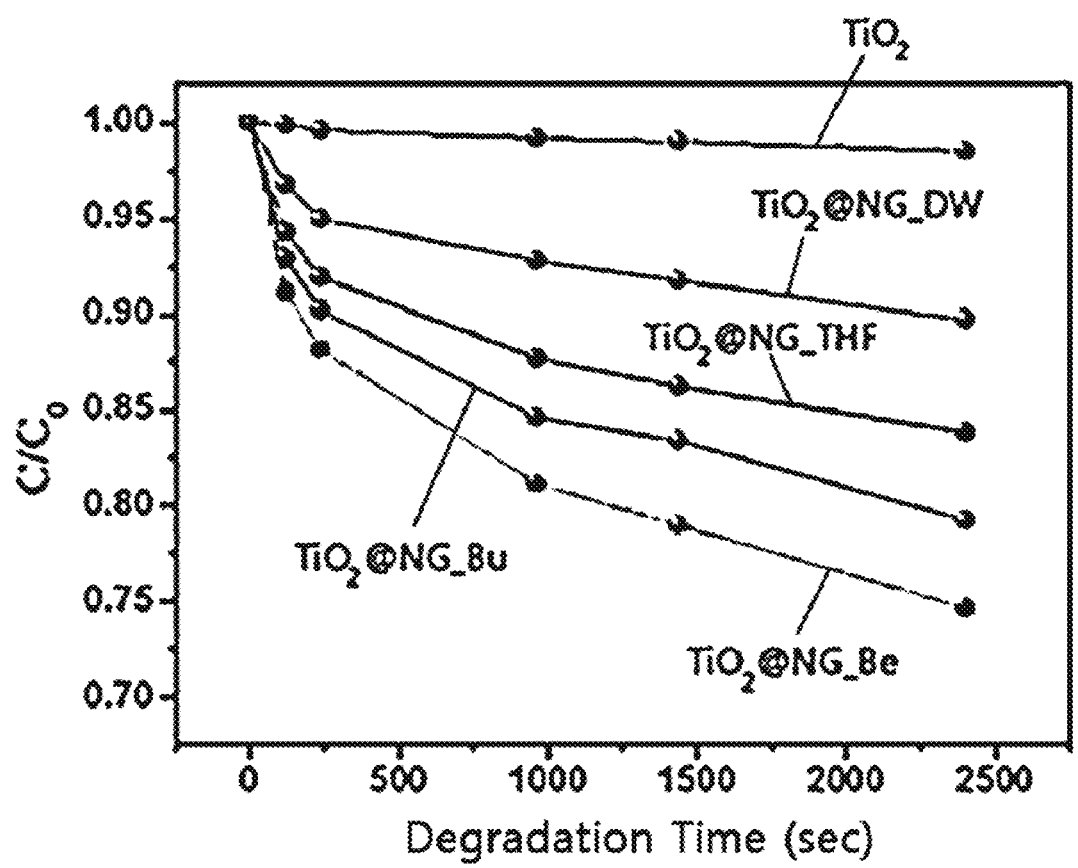
FIG. 13 shows the results of the photolysis test for organic materials carried out by using the carbon quantum dots according to Examples 6-9 and Comparative Example 2.

FIG. 13 shows a graph illustrating the relative luminance of each of the aqueous RhB solutions of the titanium dioxide photocatalyst materials (TiO$_2$@nGCDs) containing the carbon quantum dots according to Examples 6-9 and Comparative Example 2. The aqueous RhB solution is decomposed by free radicals (.O$_2^-$ or .OH$^-$) generated due to UV rays and characteristically becomes transparent. UV rays emitted from a xenon lamp are irradiated to the aqueous RhB solution. In addition, to exclude the photoactive property of titanium dioxide used as a support, a light source from which the light with a wavelength of 400 nm or less is removed through a cutoff filter is used on the basis of the fact that the light absorbance of titanium dioxide is significantly decreased in a wavelength range of 400 nm or higher. Pure titanium dioxide powder or each of the photocatalyst materials obtained from Examples 6-9 is dipped in the aqueous RhB solution, and the relative luminance of each aqueous RhB solution is determined at each time point (2 minutes, 4 minutes, 16 minutes, 24 minutes, 40 minutes), while the light source with the above-mentioned wavelength range is irradiated thereto. In other words, based on titanium dioxide powder irradiated with the same dose of light source, the luminance ratio of each aqueous RhB solution in which each of the photocatalysts is dipped is determined after the same time.

Figure 14:
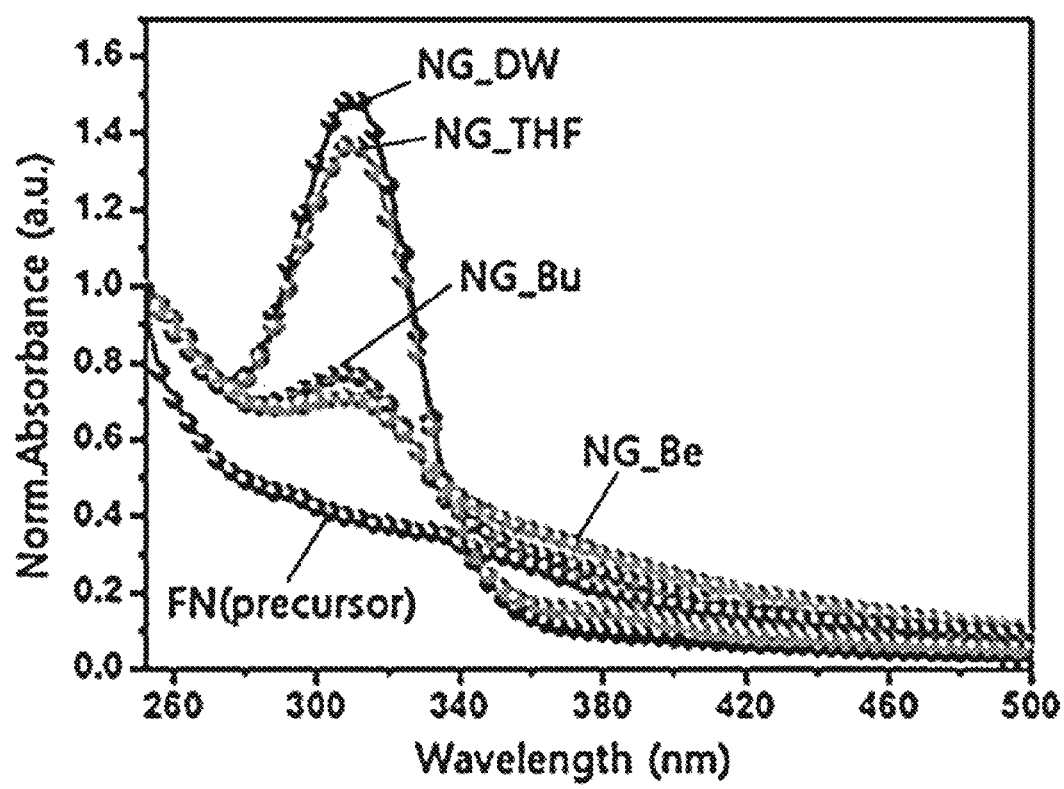
FIG. 14 shows the results of determination of absorbance for the carbon quantum dots according to Example 1-4.

It can be seen from FIG. 13 that pure titanium dioxide photocatalyst (TiO$_2$) shows a decrease in luminance of about 2.7%, when the luminance is determined after carrying out a photolysis test for 40 minutes. On the contrary, each of the photocatalyst materials according to Examples 6-9 shows a decrease in luminance of 10.3% (TiO$_2$@NG_DW), 16.2% (TiO$_2$@NG_THF), 20.8% (TiO$_2$@NG_Bu) and 25.3% (TiO$_2$@NG_Be), respectively. This suggests that each of the photocatalysts shows a photocatalytic activity improved by at least 10 times as compared to pure titanium dioxide powder in a range of UV rays of 400 nm or higher. It can be seen from FIG. 14 that the above results are based on the light absorbing ability of the carbon quantum dot itself.

Figure 15:
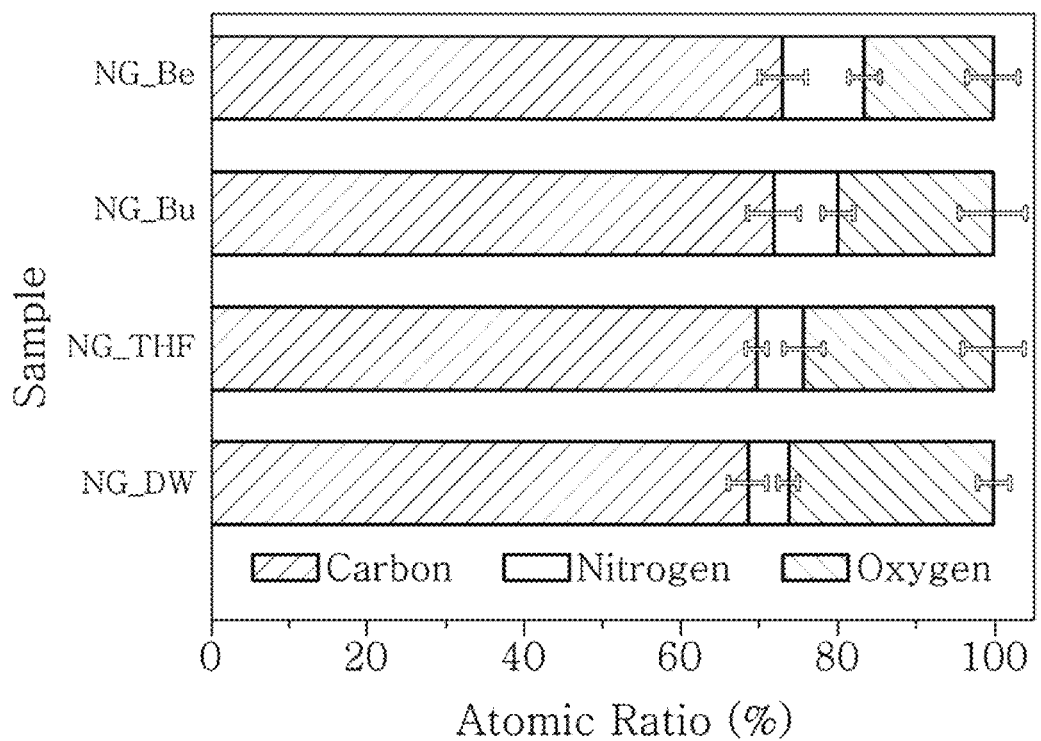
FIG. 15 shows the results of the chemical compositions of the carbon quantum dots according to Example 1-4 as determined by using X-ray photoelectron analysis.

Another basis for improvement of photocatalytic properties may be related with an increase in nitrogen content as can be seen from FIG. 15. In a carbon nanostructure, each of the heteroatoms, oxygen and nitrogen, may relatively form p type and n type domains in the structure. Therefore, as the number of the corresponding domains increases in the structure, the interfaces that may be formed by the domains are increased so that the exitons formed by the light source absorbed thereto may be separated into electrons and holes, thereby affecting a degree of generating free radicals required for a photolysis reaction.

Referring to FIG. 15, it can be seen that when using the photocatalyst materials according to Examples 6-9, the ratio of heteroatoms, oxygen and nitrogen, is high. Therefore, it is expected that the photocatalysts according to Examples 6-9 include a large number of p type and n type domains formed in the structures to generate a large number of free radicals required for a photocatalyst-based photolysis, and thus have excellent properties as photocatalysts.

What is claimed is:

1. Nitrogen-doped carbon quantum dots as pyrolysis product of fumaronitrile.

2. The carbon quantum dots according to claim 1, which are porous carbon quantum dots.

3. The carbon quantum dots according to claim 1, wherein nitrogen is doped in an amount of 3-10 wt % based on the total weight of the carbon quantum dots.

4. The carbon quantum dots according to claim 1, which have a thickness of 0.5-5 nm.

5. The carbon quantum dots according to claim 1, which have a ratio of sp2:sp3 ranging from 2.3:1 to 5.1:1.

6. The carbon quantum dots according to claim 1, which are represented by the following Chemical Formula 1:

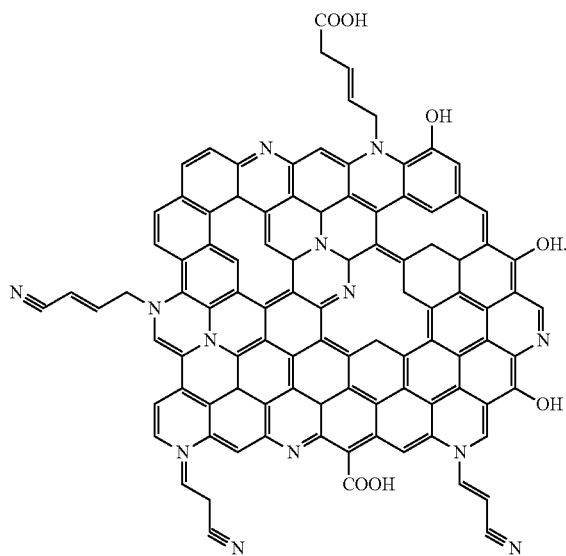

7. An organic solar cell comprising an active layer containing the carbon quantum dots as defined in claim 1.

8. The organic solar cell according to claim 7, wherein the active layer comprises the carbon quantum dots in an amount of 0.2-5 wt % based on the weight of the active layer.

9. The organic solar cell according to claim 7, which has a photoelectric conversion efficiency of 7.3-8.6%.

10. A photocatalyst comprising the carbon quantum dots as defined in claim 1.

* * * * *